United States Patent [19]

Rossall

[11] Patent Number: 5,344,647
[45] Date of Patent: * Sep. 6, 1994

[54] STRAIN OF MICROORGANISM HAVING ANTIMICROBIAL ACTIVITY

[75] Inventor: Stephen Rossall, Derby, England

[73] Assignee: Agricultural Genetics Company Limited, Cambridge, United Kingdom

[*] Notice: The portion of the term of this patent subsequent to Oct. 29, 2008 has been disclaimed.

[21] Appl. No.: 998,640

[22] Filed: Dec. 29, 1992

Related U.S. Application Data

[63] Continuation of Ser. No. 144,174, Jan. 15, 1988, abandoned.

[30] Foreign Application Priority Data

Jan. 21, 1987 [GB] United Kingdom ............... 01234

[51] Int. Cl.$^5$ ............... A61K 35/74; C12N 1/20; C12P 21/02
[52] U.S. Cl. ............... 424/93.462; 424/520; 435/252.5; 435/839
[58] Field of Search ............... 435/252.5, 839; 424/93 M, 520

[56] References Cited

U.S. PATENT DOCUMENTS

| | | | |
|---|---|---|---|
| 4,181,714 | 1/1980 | Misato et al. | 424/117 |
| 4,582,704 | 4/1986 | Baker et al. | 424/93 |
| 4,764,371 | 8/1988 | Pusey et al. | 435/839 |
| 5,061,495 | 10/1991 | Rossall | 424/520 |

FOREIGN PATENT DOCUMENTS

| | | |
|---|---|---|
| 2806813 | 2/1978 | Fed. Rep. of Germany . |
| 2508766 | 7/1981 | France . |
| 446615 | 9/1964 | Switzerland . |
| 2061284 | 10/1980 | United Kingdom . |
| 2200924 | 2/1988 | United Kingdom . |

OTHER PUBLICATIONS

McKeen, D. C., Reilly, C. C. and Pusey, P. L. *Phytopathology* (1986) 76, 136–139.

Utkhede, R. S. and Sholberg, P. L. *Canadian Journal of Microbiology* (1986) 32, 963–967.

Delcambe, L., Peypous, F., Guinard, M. and Michel, G. *Revue des Fermentations et des industries alimentaires* (1977), 147–151.

Broadbent, P., Baker, K. F. and Waterworth, Y. *Austrialian Journal of Biological Science* (1971) 24, 925–944.

Hosono, K. and Suzuki, H. Chemical Abstracts vol. 107, No. 25 (12.21.87), p. 635, abstract no. 234854m.

Swinburne, T. R., Barr, J. G. and Brown, A. E. *Transactions of the British Mycological Society* (1975) 65, 211–217.

Korzybski et al., "Antibiotics; origin, nature and properties", vol. 1, 1967, pp. 133–134, Pergamon Press, Oxford, GB.

Transact of the Brit Mycologic Soc. 60 pp. 389 to 403, 1973.

Transact. of the Brit. Mycologic Soc. 65, 211–217, 1975.

Phytopath 58 pp. 1395 to 1401, 1968.

Phytopath 58 pp. 79 to 87, 1968.

*Primary Examiner*—Jacqueline Stone
*Attorney, Agent, or Firm*—Oblon, Spivak, McClelland, Maier & Neustadt

[57] ABSTRACT

The invention provides *Bacillus subtilis* strains NCIB 12375, NCIB 12376 and NCIB 12616, which have improved antimicrobial activity. The invention also relates to the use of such strains in the control of microbial infections and microbial contamination.

21 Claims, 1 Drawing Sheet

○ = control
■ = sprayed with Bs 3.6 3d before inoculation
▲ = sprayed with Bs RI 3d before inoculation
▼ = sprayed with Bs 3.6 simultaneously with inoculation
● = sprayed with Bs 3 6 7d after inoculation

STRAIN OF MICROORGANISM HAVING ANTIMICROBIAL ACTIVITY

This application is a continuation of application Ser. No. 07/144,174, filed on Jan. 15, 1988, now abandoned.

This invention relates to a strain of *Bacillus subtilis* having antimicrobial activity.

*Bacillus subtilis* is a spore-forming, aerobic, highly resilient, flagellated bacterium. It has been the subject of a great deal of biological control research and promising results have been reported in various trials on, for example Rhizoctonia and Pythium damping off (Olsen 1964, Olsen and Baker 1968, Broadbent et al 1971), *Nectria galligena* infection of leaf scars on apple trees (Swinburne 1973), Fusarium seedling blight in wheat (Chang and Kommedahl 1968). *B. subtilis* also has the advantage of being easy and cheap to produce, requiring only simple growth media.

We have isolated a new strain of *B. subtilis* during screening of bacteria from the leaf surface of faba bean plants grown in field plots at Sutton Bonington. The new strain has been found to have surprising antimicrobial activity on various bioassays.

The invention thus provides *Bacillus subtilis* strain (JB 3), a sample of which has been deposited on 22 December 1986 at The National Collections of Industrial Bacteria Ltd (NCIB), Tory Research Station, P.O. Box 31, 135 Abbey Road, AB9 8DG, Scotland, under accession number NCIB 12375, or a mutant or derivative thereof having antimicrobial activity.

A particularly effective mutant or derivative of strain JB 3 is strain JB 3.6, a sample of which has been deposited on 22 December 1986 at NCIB under accession number NCIB 12376.

Another particularly effective mutant or derivative of strain JB 3 is strain R1, a sample of which has been deposited on 24 December 1987 at NCIB under accession number NCIB 12616.

The invention also relates to the use of the above strains or derivatives or mutants thereof, or antimicrobial materials derived from these strains or derivatives or mutants thereof, in controlling plant diseases, microbial infections of animals and humans and in controlling microbial contamination generally. The new strains can optionally be used in mixtures with other microbial strains.

The new strains are particularly useful in controlling plant fungal diseases. For application to plants, the strains may be formulated into compositions containing suitable carriers or diluents. In order to ensure wettability of plant leaves during application, the compositions may contain gums or surfactants.

In in-vitro bioassays the new strain was found to have antifungal activity against a wide range of fungal pathogens, causing marked distortion of germ tubes, lysis of the hyphal tips and subsequent death of the fungi. Fungi tested so far include:
Alternaria spp.
Botrytis spp.
Leptosphaeria spp.
Rhizoctonia spp.
Sclerotinia spp.
Ascochyta spp.
Candida spp.
Experiments with whole plants have demonstrated control of rust infections (e.g. Puccinia spp.)

Antibacterial activity was found in in-vitro tests against organisms such as:
Staphylococcus spp.
Streptococcus spp.

In glasshouse tests with intact faba bean and barley plants, spraying with a suspension of the *B. subtilis* strain effectively prevented the development of symptoms when the leaves were subsequently inoculated with *Botrytis fabae* or *Puccinia hordei* respectively.

The antimicrobial activity is produced under nutrient-limiting conditions which are commonly associated with the process of sporulation. It is anticipated that wetting and drying cycles on the leaf surface would result in cycles of germination and sporulation of *B. subtilis* and consequent production of antimicrobial activity. Unlike some antimicrobial activities of *B. subtilis*, the new activity is very stable, remaining active even after autoclaving.

Much antimicrobial activity is merely produced as an artefact of axenic culture on synthetic media. However, it is highly likely that this activity is actually produced on leaf surfaces. Young cultures of the bacterium (12 - 18 h) which showed no detectable antimicrobial activity provided effective disease control when applied to infected leaves. On microscopic examination the pathogens showed identical distorted growth to that observed in vitro.

The following characteristics of the new strain were noted:

| | Tests at 30° C. | |
|---|---|---|
| Spore shape: | Elliptical or cylindrical | (Maximum growth temp 50° C.) |
| Sporangium distended distinctly: | — | |
| Spore position dominant: | Central | |
| Rod width, μm | 1 | |
| Intracellular globules (a) | — | |
| Anaerobic growth (a) | (+) (weakly positive) | |
| Growth in 5% NaCl | + | |
| Growth in 7% NaCl | + | |
| Growth in pH 5.7 broth | + | |
| Acid from glucose (b) | + | |
| Gas from glucose (b) | — | |
| VP (acetoin) | + | |
| Egg Yolk agar opacity | — | |
| Casein decomposition | + | |
| Gelatin decomposition | + | |
| Starch hydrolysis | + | |
| $NO_3^-$ to $NO_2^-$ | + | |
| Aesculin hydrolysis | + | |
| Citrate, Koser's | + | |
| Arginine dihydrolase Moller's | — | |
| pH in VP broth | 5.2 | |

(a) on glucose agar
(b) peptone water sugar, Andrade's indicator

Acid was produced from the following carbon sources at 30° C.:

Glycerol, L-arabinose, ribose, D-xylose, galactose, D-glucose, D-fructose, D-mannose, inositol, mannitol, sorbitol, α-methyl-D-glucoside, N-acetyl glucosamine, amygdalin, arbutin, salicin, cellobiose, maltose, lactose, melibiose, sucrose, trehalose, inulin, D-raffinose, starch, glycogen, β-gentiobiose, D-turanose.

The invention is illustrated by the following Examples, and by the accompanying drawing showing the results of Example 4B.

EXAMPLE 1

Isolation of the novel strain

The bacterium was isolated from plots of faba bean grown at the Nottingham University School of Agriculture at Sutton Bonnington.

Preliminary experiments indicated considerable variation on the development of chocolate spot disease (*Botrytis fabae*) on leaves removed from field plots. This may have been a reflection of differences in the leaf surface microflora. Isolations of potential antagonists of plant pathogens were therefore made from leaves shown to permit only limited disease development.

Bifoliate leaves were detached and one leaflet of each pair was inoculated with *Botrytis cinerea* and *Botrytis fabae*. After 24h incubation microorganisms were isolated from the leaflets opposite those with low disease scores and tested for antifungal activity. Repeated isolations were made after shaking 2-3 leaflets in 50 ml aliquots of sterile distilled water for 30 minutes. Bacteria were isolated by plating out washings onto nutrient agar containing nystatin to suppress fungal growth. After 48-72 h incubation, cells from individual colonies were streaked onto one side of plates of V8 juice agar and grown at 30° C. for 3 days. The opposite side of the agar was inoculated with a plug of *Botrytis cinerea* and following incubation antimicrobial activity was indicated by a zone of inhibition of fungal growth compared to controls. Such antimicrobial activity was associated with several colonies of one bacterial species subsequently identified as *Bacillus subtilis*. One of these colonies was designated as JB 3.

Serial dilutions of the bacterial cells derived from pure cultures of JB 3 were plated onto nutrient agar. Plates with 1-50 discrete colonies were selected for isolation of single-cell cultures. A total of 22 such isolates were made and tested for antimicrobial activity. Point inoculation of plates of V8 agar seeded with conidia of *Botrytis cinerea* were made from individual colonies. After 72h incubation zones of inhibition of fungal growth were measured. One isolate (designated JB3.6) produced an inhibitory zone much larger than any other isolate tested and this was used extensively in subsequent tests.

EXAMPLE 2

In vitro Anti-Fungal Bioassays

Simultaneous inoculations of *B. subtilis* strain JB 3.6 and the test fungus were made onto potato dextrose agar plates. Two *B. subtilis* streaks, 1 cm long, were made 1 cm from diametrically opposite sides of each plate. A 0.5 cm mycelial plug of the test fungus was placed in the middle. Control plates had no *B. subtilis* inoculation. Plates were incubated at 25° C. for up to 12 days. The diameter of each fungal colony, on a line through the centre of the mycelial plug at right angles to the streaks of *B. subtilis*, was measured daily. Percentage reduction of fungal growth was calculated with reference to the test colony diameter at the time when the corresponding control plate showed a full cover of fungus, i.e. when the control colony diameter was 90 mm. The results are shown in Table 1.

TABLE 1

| Taxonomic Group. | Test Fungus | Final colony diameter (mm) | % reduction in growth | Morphological effects | Casual agent of: |
| --- | --- | --- | --- | --- | --- |
| Phycomycetes | *Phytophthora capsici* | 90.0 | 0% | None | Capsicum rot |
|  | *Pythium ultimum* | 90.0 | 0% | None | Damping-off |
| Zygomycetes | *Absidia glauca* | 51.0 | 43% | Swelling & lysis* | Non-pathogen |
| Ascomycetes | *Sordaria fimicola* | 56.5 | 37% | Swelling* | Non-pathogen |
| Imperfecti | *Alternaria brassicae* | 35.0 | 61% | Swelling & lysis* | Leaf spot of brassicas |
|  | *Botrytis cinerea* | 46.5 | 48% | " | Grey mould etc |
|  | *Botrytis fabae* | 49.0 | 46% | " | Chocolate spot of bean |
|  | *Fusarium oxysporum* | 76.0 | 0% | " | Vascular wilts |
|  | *Monilinia fructigena* | 67.0 | 26% | " | Brown rot apple |
|  | *Penicillium chrysogenum* | 57.0 | 37% | " | Non-pathogen |
|  | *Phialophora radicola* | 35.5 | 61% | " | Non-pathogen |
|  | *Leptospaeria muculans* | 27.5 | 64% | " | Oilseed rape canker |
|  | *Rhizoctonia solani* | 51.0 | 43% | " | Damping-off |
|  | *Monilinia laxa* | 43.5 | 52% | " | Brown rot apple |
|  | *Trichodernam harzianum* | 57.5 | 36% | " | Non-pathogen |

*Fungi probably dead.

In similar tests activity of *B. subtilis* strain JB 3.6 was also demonstrated against the following fungi:
*Botrytis allii*
*Botrytis elliptica*
*Botrytis narcissicola*
*Botrytis tulipae*
*Ascochtya fabae*
*Cladosporium herbarum*
*Saccharomyces cerevisiae*
*Candida albicans*

EXAMPLE 3

In vitro anti-bacterial bioassays

Nutrient agar plates were seeded with the test bacteria and streaked with *B. subtilis* strain JB 3.6. Plates were incubated at 30° C. for 24h and the presence or absence of zones of inhibition around the *B. subtilis* streak was recorded.

*B. subtilis* produced zones of inhibitions when tested against the following bacteria:
*Staphylococcus aureus*
*Streptococcus lactis*
*Strepococcus agalactiae*
*Micrococcus luteus*
*Micrococcus roseus*
*Bacillus megaterium*

EXAMPLE 4

Biological control of chocolate spot (*Botrytis fabae*) on faba bean by *Bacillus subtilis* (JB 3.6)

Part A

Four replicate plots (1 x 2 m) were used for each treatment with 1 m guard rows. The following treatments were used.

A. Plants inoculated by spraying with mixed isolate spore suspension of *Botrytis fabae* ($10^5$ spores $ml^{-1}$) in nutrient solution on day 0 - i.e. control.

B. Plants inoculated with *Botrytis fabae* and a suspension of *Bacillus subtilis* cells (JB 3.6) (18h culture) on day 0.

C. Plants inoculated as B, followed by a repeat spray of *B. subtilis* cells (18h culture) on day 7.

D. Plants inoculated with *Botrytis fabae* and a suspension of *B. subtilis* cells (72h culture) on day 0.

E. Plants inoculated as D, followed by a repeat spray of *B. subtilis* cells (72h culture on day 7).

The experiment was designed as a randomized block. Prior to inoculation 5 plants were randomly selected from within each treatment block and tagged. Disease assessments were made on these plants by estimating the area of leaf which had turned brown/black on leaves 3-5. Mean values of % disease were then calculated. This procedure was considered more accurate than attempting to assign a somewhat subjective score for the whole plot. Results obtained as given in Table 2.

These results show that a significant level of control was achieved by 2d and maintained for the 14d duration of the experiment using 18h- or 72h culture of *B. subtilis*. Recording ceased after 14d as many control plot leaves had reached 100% disease and abscised. However observations made after this period indicated no further disease development on plots treated with *B. subtilis* for several weeks. By 4d the 72h bacterial culture gave more effective control than the 18h culture which permitted limited infection to occur before antibiotic production occurred. Microscopic examination of inoculated tissues indicated typical distortion of fungal germ tubes. A second spray with *B. subtilis* at 7d caused no significant improvement in control, possibly reflecting the death of the pathogen before this stage.

TABLE 2

Disease development on faba bean following inoculation with *Botrytis fabae* in presence and absence of *Bacillus subtilis* strain JB 3.6

| | Disease score (DS) and % disease reduction (% R) | | | | | | | | | |
|---|---|---|---|---|---|---|---|---|---|---|
| | Day 2 | | Day 4 | | Day 7 | | Day 10 | | Day 14 | |
| | DS | % R | DS | % R | DS | % R | DS | % R | DS | % R |
| A | 18.9 | — | 40.7 | — | 59.0 | — | 66.7 | — | 70.3 | — |
| B | $2.2^a$ | 88.4 | $7.9^a$ | 80.6 | $17.7^a$ | 70 | $18.9^a$ | 71.7 | $19.6^a$ | 72.1 |
| C | $1.6^a$ | 91.5 | $7.8^a$ | 80.8 | $13.9^a$ | 76.4 | $17.6^a$ | 73.6 | $18.3^a$ | 74.0 |
| D | $0.5^a$ | 97.4 | $1.4^{ab}$ | 96.6 | $5.0^{ab}$ | 91.5 | $6.7^{ab}$ | 90.0 | $71.1^{ab}$ | 89.9 |
| E | $0.2^a$ | 98.9 | $1.4^{ab}$ | 96.6 | $2.7^{ab}$ | 95.4 | $4.9^{ab}$ | 92.7 | $5.3^{ab}$ | 92.5 |

$a$ = significantly less than control (p = 0.001) by student 't' test (mean of 60 replicates)
$b$ = significantly less than treatments B and C (p = 0.001) by student 't' test

Part B

The efficacy of *B. subtilis* 3.6 in the control of Botrytis infection of bean in a polythene tunnel was further tested as follows. An overhead mist-irrigation system was installed to provide an environment highly suited to disease development, and a dwarf bean variety was used to reduce problems of lodging, which can occur in polytunnels. Four replicate plots were used for each treatment and the timing of application of the biocontrol agent was tested. *B. subtilis* 3.6 was applied to plots 3d before, simultaneous with and 7d after the application of *Botrytis fabae* spore suspension. By 7d the disease was beginning to develop symptoms. A further treatment used the rifampicin resistant strain of *B. subtilis* R1 (see Example 7) to monitor bacterial survival. Data for biological control are given in the accompanying drawing, which is a graph of percentage infection against time after inoculation. Mean disease scores represent the area of the fourth leaf infected in 10 randomly selected plants in each of the 4 replicate plots. Excellent control was obtained when bacteria were applied prophylactically before and simultaneously with the patbogen. The control agent also possessed the ability to greatly reduce disease when applied after infection had begun. Control was maintained for the 36d period of the experiment, by which time many of the leaves in control plots had abscinded.

EXAMPLE 5

Control of Cladosporium fulvum infection of tomato

Four-week-old tomato seedlings were inoculated with the leaf mould patbogen in the presence or absence of *B. subtilis* JB 3.6. Plants were sprayed with a Bacillus 72h culture, left to dry, then sprayed with a suspension of Cladosporium spores. After enclosure in clear polythene bags for 48h, the plants were maintained in the glasshouse for 3 weeks. The percentage leaf area infected was assessed for leaves 1-3 and data obtained are given in Table 3. It is clear that Bacillus has reduced infection even though the experiment was performed under conditions that are disadvantageous for biological control agents. For instance, the inoculation procedure for this Cladosporium involves repeated spraying of whole plants; the likelihood of wash-off of the control agent must therefore be considered. Moreover, due to the extreme hemibiotrophic nature of this fungus, disease symptoms take a long time to appear.

TABLE 3

The effect of *B. subtilis* JB 3.6 in development of *Cladosporium fulvum* infection of tomato

| Leaf number | Percentage leaf area infected 21d after inoculation $a$ | |
|---|---|---|
| | Control | +Bs JB 3.6 |
| 1 | 26.8 | 5.7 |
| 2 | 5.9 | 2.1 |
| 3 | 0.4 | 0.1 |

$a$ = Mean of 15 replicate plants

EXAMPLE 6

Control of Ascochyta pisi infection of pea

Three-week-old pea plants were spray inoculated with the leaf-spotting pathogen *Ascochyta pisi*. Half the population received a simultaneous inoculation with a 72h culture of *B. subtilis* JB 3.6. After 10 days growth the percentage infection was estimated on leaves 1–5 and stems; the data obtained (Table 4) show a clear reduction in disease levels. Control was most dramatic on younger leaves and stems. The treated plants tended to be considerably larger, probably reflecting the almost total absence of stem lesions. Owing to the extreme inwetability of pea plants these findings are especially interesting.

TABLE 4

The effect of *B. subtilis* JB 3.6 on development of *Ascochyta pisi* infection of pea

| Leaf number | Percentage leaf area infected 10d after inoculation[a] | |
|---|---|---|
| | Control | +Bs JB 3.6 |
| 1 | 100.0 | 92.3 |
| 2 | 100.0 | 87.7 |
| 3 | 98.3 | 26.9 |
| 4 | 75.8 | 18.5 |
| 5 | 36.7 | 2.7 |
| STEM | 28.3 | 0.9 |

[a] = Mean of 36 replicate plants

EXAMPLE 7

Control of Take-All of Wheat

Preliminary experiments on take-all of wheat caused by *Gauemannomyces graminis* have been undertaken. *B. subtilis* R1 (a rifampicin-resistant strain-derived from Bs 3.6) has been used for these experiments as this will permit future experiments on the survival of the antagonist in soil. Initial, small scale experiments on biological control coated wheat seeds with approximately $5 \times 10^7$ cfu/seed. Coated and untreated seeds were sown in compost amended with the Gauemannomyces grown on oat kernels. After incubation for 4 weeks the plants were destructively assessed for take-all infection of roots and stem bases. The results obtained are given in Table 5 which shows significant reduction in this difficult-to-control disease.

A rifampicin resistant strain was isolated by agar diffusion bioassays using Oxoid Multodiscs containing 5 μg rifampicin. A 1 ml aliquot of a 24 hour nutrient broth culture of *B. subtilis* JB 3.6 was spread onto a nutrient agar plate containing the Multodisc and allowed to dry. Single colonies growing in the zone of inhibition were selected. One of these strains was designated R1.

TABLE 5

The effect of seed application of *B. subtilis* R1 on development of take-all of wheat

| Seed treatment | Percentage plants developing stem lesions[a] |
|---|---|
| Untreated | 77.8 |
| SDW[b] wash | 66.7 |
| 1% methyl cellulose | 77.8 |
| 2.5% methyl cellulose | 50.0 |
| BsR1 in SDW | 16.7 |
| BsR1 in 1% methyl cellulose | 28.6 |
| BsR1 in 2.5% methyl cellulose | 14.3 |

[a] = Mean of 12 plants
[b] = Sterile distilled water

EXAMPLE 8

Control of Peronospora infection of oilseed rape

Downy mildew infection caused by Peronospora is an example of a biotrophic fungal disease. As such in vitro bioassays against this pathogen cannot be done. Preliminary experiments have therefore been carried out to attempt to reduce incidence of disease on oilseed rape by application of *B. subtilis* JB 3.6. Cotyledons were sprayed with sporangia of Peronospora; a simultaneous application of 72h culture of Bacillus was made to half the population. Plants were incubated under clear plastic propagators for 5d when the percentage area of cotyledons infected was estimated. Disease levels were reduced to less than half the control by the antagonist. Peronospora on oilseed rape is a pathogen of minor importance. However, other downy mildews (e.g. grape vine) and the closely related pathogens Phytophthora and Pythium, which are difficult to control existing methods, cause serious economic losses.

EXAMPLE 9

Control of Powdery mildew on cereals

Powdery mildews (*Erysiphe graminis*) on cereals probably represent the most economically damaging diseases of crop plants in Britain. Despite extensive plant breeding programmes and chemical control strategies these highly specialized pathogens still cause significant losses. Their biotrophic nature precludes in vitro bioassays. Glasshouse trials on control of mildew on wheat have been performed. Application of 72h cultures of *B. subtilis* JB 3.6 to wheat plants was given by three sprays immediately prior to inoculation with mildew. Plants were inspected 14 days after inoculation; the results (Table 6) show that application of *B. subtilis* significantly reduced disease symptoms on leaves.

TABLE 6

The effect of *B. subtilis* JB 3.6 on development of mildew infection of wheat.

| Leaf number | Percentage leaf area infected 14 d after inoculation | |
|---|---|---|
| | Control | + Bs JB 3.6 |
| 1 | 51.0 | 16.6 |
| 2 | 32.8 | 8.8 |

A problem with biological control of cereal diseases is that bacterial cultures fail to effectively wet cereal leaves and run-off of the control agent can occur. This can lead to problems with reproducibility of results. We have shown that these problems can be overcome by adding "sticker" compounds such as surfactants, to the bacterial culture. These compounds can prevent run-off of the control agent from the leaves. Results obtained using one such compound, Ethylan CD107, are shown in Table 7. In a glasshouse trial wheat plants were sprayed with 72h cultures of *B. subtilis* JB 3.6 immediately prior to inoculation with mildew. Some plants were sprayed with cultures containing 0.1% Ethylan CD107. Plants were inspected 10 days after inoculation; the results show that addition of Ethylan CD107 significantly improved disease control.

TABLE 7

The effect of Ethylan CD107 on control of mildew infection of wheat by *B. subtilis* JB 3.6.

| Leaf number | Percentage leaf area infected 10 d after inoculation | | |
|---|---|---|---|
| | Control | + BS JB 3.6 | + BS JB 3.6 + Ethylan CD107 |
| 1 | 18.2 | 18.9 | 1.4 |

References

Broadent P, Baker K. F, Waterworth Y. 1971 Bacteria and actinomycetes antagonistic to fungal root pathogens in Australian soils. Australian Journal of Biological Science, 24:925–944

Chang I P, Kommedahl T. 1968 Biological control of seedling blight of corn by coating kernals with antagonistic microorganisms. Phytopathology 58: 1395–1401

Olsen C M 1964 Antagonistic effects of microorganisms on *Rhizoctonia solani* in soil. PhD thesis, University of California Berkeley. 152 pp Olsen C M, Baker K F, 1968 Selective heat treatment of soil, and its effect on the inhibition of *Rhizoctonia solani* by *Bacillus subtilis* Phytopathology 58:79–87

Swinburne T R 1973 Microflora of apple leaf scars in relation to infection by *Nectria galligena*. Transactions of the British Mycological Society 60:389–403

I claim:

1. A biologically pure culture of *Bacillus subtilis*, Strain JB 3, a sample of which has been deposited at the National Collections of Industrial Bacteria Ltd. (NCIB) on 22 December 1986 under accession number NCIB 12375, or a mutant thereof having the same antimicrobial activity as the said strain.

2. A biologically pure culture of *Bacillus subtilis* strain JB 3.6, a sample of which has been deposited at the National Collections of Industrial Bacteria Ltd. (NCIB) on 22 December 1986 under accession number NCIB 12376, or a mutant thereof having the same antimicrobial activity as the said strain.

3. A biologically pure culture o *Bacillus subtilis* strain R1, a sample of which has been deposited at the National Collections of Industrial Bacteria Ltd. (NCIB) on 24 December 1987 under the accession number NCIB 12616 or a mutant thereof having the same antimicrobial activity as the said strain.

4. An antimicrobial composition comprising a biologically pure culture of *Bacillus subtilis* strain JB 3, or JB 3.6, or R1, or a mutant of any of such strains, said mutant having the same antimicrobial activity as the said strain, or antimicrobial material isolated from any of such strains, together with a carrier or diluent therefor.

5. The antimicrobial composition according to claim 4, comprising a biologically pure culture of *Bacillus subtilis* strain JB 3, or a mutant thereof having the same antimicrobial activity as the said strain, or said antimicrobial material isolated from such strain.

6. The antimicrobial composition according to claim 4, comprising a biologically pure culture of *Bacillus subtilis* strain JB 3.6, or a mutant thereof having the same antimicrobial activity as the said strain, or said antimicrobial material isolated from such strain.

7. The antimicrobial composition according to claim 4, comprising a biologically pure culture of *Bacillus subtilis* strain R1, or a mutant thereof having the same antimicrobial activity as the said strain, or said antimicrobial material isolated from such strain.

8. A method of controlling microbial infections in plants, which comprises applying to the plants or their environment *Bacillus subtilis* strain JB 3, or JB 3.6, or R1, or a mutant of any of such strains, said mutant having the same antimicrobial activity as the said strain, or an antimicrobial composition according to claim 4.

9. The method of claim 4, comprising applying to said plants or their environment *Bacillus subtilis* strain JB 3, or a mutant thereof having the same antimicrobial activity as the said strain, or said antimicrobial material isolated from such strain.

10. The method of claim 8, comprising applying to said plants or their environment *Bacillus subtilis* strain JB 3.6, or a mutant thereof having the same antimicrobial activity as the said strain, or said antimicrobial material isolated from such strain.

11. The method of claim 8, comprising applying to said plants or their environment *Bacillus subtilis* strain R1, or a mutant thereof having the same antimicrobial activity as the said strain, or said antimicrobial material isolated from such strain.

12. The biologically pure culture of *Bacillus subtilis* according to claim 1, which is in a form suitable for use in control of microbial infection or microbial contamination.

13. The biologically pure culture of *Bacillus subtilis* according to claim 2, which is in a form suitable for use in control of microbial infection or microbial contamination.

14. The biologically pure culture of *Bacillus subtilis* according to claim 3, which is in a form suitable for use in control of microbial infection or microbial contamination.

15. The antimicrobial composition according to claim 4, also including a gum or surfactant.

16. The antimicrobial composition according to claim 15, which is in a form suitable for use in control of microbial infection or microbial contamination.

17. The antimicrobial composition according to claim 4, which is in a form suitable for use in control of microbial infection or microbial contamination.

18. The method of claim 8, wherein said antimicrobial composition further comprises a gum or surfactant.

19. The method of claim 9, wherein said antimicrobial composition further comprises a gum or surfactant.

20. The method of claim 10, wherein said antimicrobial composition further comprises a gum or surfactant.

21. The method of claim 11, wherein said antimicrobial composition further comprises a gum or surfactant.

* * * * *